United States Patent
Shao

(10) Patent No.: US 10,905,793 B2
(45) Date of Patent: Feb. 2, 2021

(54) BONE CEMENT COMPOSITION KIT

(71) Applicant: DRAGON CROWN MEDICAL CO., LTD., Shandong (CN)

(72) Inventor: Wei-Xing Shao, Shandong (CN)

(73) Assignee: DRAGON CROWN MEDICAL CO., LTD., Shandong (CN)

(*) Notice: Subject to any disclaimer, the term of this patent is extended or adjusted under 35 U.S.C. 154(b) by 0 days.

(21) Appl. No.: 16/042,382

(22) Filed: Jul. 23, 2018

(65) Prior Publication Data

US 2019/0076570 A1 Mar. 14, 2019

(30) Foreign Application Priority Data

Sep. 8, 2017 (CN) .......................... 2017 1 0805590

(51) Int. Cl.
*A61L 24/06* (2006.01)
*A61L 24/00* (2006.01)
*A61L 24/04* (2006.01)
*A61L 24/02* (2006.01)

(52) U.S. Cl.
CPC ....... *A61L 24/0094* (2013.01); *A61L 24/0031* (2013.01); *A61L 24/0089* (2013.01); *A61L 24/02* (2013.01); *A61L 24/043* (2013.01); *A61L 24/06* (2013.01); *A61L 2400/06* (2013.01); *A61L 2430/02* (2013.01)

(58) Field of Classification Search
CPC ..................................................... A61L 24/06
See application file for complete search history.

(56) References Cited

U.S. PATENT DOCUMENTS

| | | | | |
|---|---|---|---|---|
| 4,490,497 A | * | 12/1984 | Evrard | A61K 6/083 523/116 |
| 5,902,839 A | | 5/1999 | Lautenschlager et al. | |
| 6,800,245 B1 | | 10/2004 | Erbe et al. | |
| 8,575,274 B2 | | 11/2013 | Hasenwinkel et al. | |
| 2010/0256647 A1 | | 10/2010 | Trieu et al. | |
| 2013/0210960 A1 | * | 8/2013 | Lee | A61L 24/0015 523/116 |
| 2015/0081034 A1 | * | 3/2015 | Mikos | A61L 27/16 623/23.61 |

FOREIGN PATENT DOCUMENTS

| | | |
|---|---|---|
| CN | 103221121 A | 7/2013 |
| CN | 104511054 A | 4/2015 |
| CN | 106390192 A | 2/2017 |
| WO | 2009129221 A1 | 10/2009 |

OTHER PUBLICATIONS

Search report from related Taiwan application 10613572, dated Apr. 9, 2018.
English translation of the search report from related Taiwan application 10613572, dated Mar. 29, 2018.
Office Action from CNIPA dated Apr. 17, 2019 for related CN application 201710805590.9.
English Abstract Translation of Foreign Patent Document CN104511054A.
English Abstract Translation of Office Action, dated Aug. 17, 2019.
Office Action from CNIPA dated May 27, 2020 for related CN application 201710805590.9.
English Abstract Translation of Office Action from CNIPA dated May 27, 2020 for related CN application 201710805590.9.
English Abstract Translation of Foreign Patent Document CN106390192A.
Office Action dated Dec. 4, 2020 issued by China National Intellectual Property Administration for counterpart application No. 201710805590.9.
"Collection of Chinese Surgery Experts' Experience" p. 315.

* cited by examiner

*Primary Examiner* — Michael F Pepitone
(74) *Attorney, Agent, or Firm* — WPAT, P.C., Intellectual Property Attorneys; Anthony King

(57) ABSTRACT

The present invention provides a bone cement composition kit. The bone cement composition kit includes a bone matrix component and a hydrogel component, respectively stored in separate containers, wherein the bone matrix component includes a bone matrix, the hydrogel component includes an acrylic polymer and an acrylic monomer. A ratio of the bone matrix component to the hydrogel component is in a range from about 1:2 (mL/mL) to about 1:50 (mL/mL).

14 Claims, No Drawings

BONE CEMENT COMPOSITION KIT

BACKGROUND

The present disclosure is related to the field of orthopedics; in particular, to bone cement composition kits.

Percutaneous vertebroplasty is a minimally invasive, image-guided surgery that involves passing a bone biopsy needle from the pedicle into the vertebral body experiencing the compression fracture, followed by the injection of a bone cement, thereby preventing the continual collapse of the vertebral body. Currently, poly(methyl methacrylate) (PMMA)-based bone cement is the most common bone cement composition. However, such PMMA-based bone cement compositions do not possess the in vivo activity for bone bonding; that is, said PMMA-based bone cement cannot form a chemical bond with the human bone tissue or cannot be replaced with the newly formed bones; therefore, the interface between the bone cement and the bone may be disrupted after long-term use, thereby causing the risk of disengagement.

In view of the foregoing, one purpose of the present disclosure is to provide an inorganic bone substitute capable of inducing osteogenesis (i.e., bone tissue formation). The conventional PMMA-based bone cement is disadvantageous in that it is non-biodegradable, non-porous, and unfavorable to the growth of the bone cells, and the present disclosure provides a novel bone cement containing a mixture of the inorganic bone substitute and the PMMA-based bone cement, thereby ameliorate the above-mentioned issues.

BRIEF SUMMARY OF THE INVENTION

One purpose of the present disclosure is to provide a bone cement composition kit, which comprises a bone matrix component and a hydrogel component, respectively stored in separate containers, wherein the bone matrix component comprises a bone matrix, the hydrogel component comprises an acrylic polymer and an acrylic monomer, and the ratio of the bone matrix component to the hydrogel component is in a range from about 1:2 (ml/ml) to about 1:50 (ml/ml).

Another purpose of the present disclosure is to provide a method of treating a bone defect by administrating to a bone region with a defect the bone cement composition kit according to the present disclosure.

As compared with the conventional poly(methyl methacrylate) (PMMA)-based bone cement that is non-biodegradable, non-porous, and unfavorable to the growth of the bone cells, the bone cement composition kit according to embodiments of the present disclosure addresses said disadvantages by incorporating a bone matrix that is osteogenic into the conventional PMMA-based bone cement so as to facilitate the bone tissue formation.

According to various embodiments of the present disclosure, the mechanical properties of the present bone cement composition kit can be altered by adjusting the ratio between the bone matrix component containing the bone matrix and the hydrogel component comprising the acrylic polymer and the acrylic monomer; accordingly, the bone cement composition kit according to the present disclosure may be applied in varies orthopedic surgeries, such as, percutaneous vertebroplasty, arthroplasty, craniofacial repair, etc.

The following disclosure provides several different embodiments, or examples, for implementing different features of the present invention. As could be appreciated, these are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

As used herein, the term "vehicle" refers to a pharmaceutically-acceptable inactive substance, which is used to assemble to the bone matrix to enable or promote the manufacture, administration, delivery, and adherence of the bone matrix, thereby facilitating the absorption of the bone matrix in a mammalian subject.

As used herein, the terms "injected," "injection," or "injectable" refer to the administration of any polymer, including injection, immersion or delivery to a subject via any delivery means.

According to one embodiment, in the bone cement composition kit of the present disclosure, the ratio of the bone matrix component to the hydrogel component is in a range from about 1:2 (ml/ml) to about 1:50 (ml/ml). Preferably, the ratio of the bone matrix component to the hydro gel component is in a range from about 1:4 (ml/ml) to about 1:20 (ml/ml). More preferably, the ratio of the bone matrix component to the hydrogel component is in a range from about 1:4 (ml/ml) to about 1:10 (ml/ml).

According to one embodiment, in the bone cement composition kit of the present disclosure, the ratio of the acrylic polymer to the acrylic monomer is in a range from about 1:10 (g/g) to about 20:1 (g/g). Preferably, the ratio of the acrylic polymer to the acrylic monomer is in a range from about 1:6 (g/g) to about 4:1 (g/g). More preferably, the ratio of the acrylic polymer to the acrylic monomer is in a range from about 1:4 (g/g) to about 2:1 (g/g).

According to one embodiment, in the bone cement composition kit of the present disclosure, the bone matrix can be an inorganic bone substituent that is osteogenic; for example, the bone matrix may have a main constituent that is a phosphate, sulfate, bioglass ($Na_2O$—$CaO$—$SiO_2$—$P_2O_5$) or a mixture thereof.

According to one embodiment, the main constituent is a phosphate selected from the group consisting of, hydroxyapatite (HA), β-tricalcium phosphate (β-TCP), tetracalcium phosphate, calcium hydrogen phosphate (CaHPO$_4$), octacalcium phosphate (Ca$_8$H$_2$(PO$_4$)$_6$·5H$_2$O), calcium pyrophosphate (Ca$_2$P$_2$O$_7$), amorphous calcium phosphate (ACP), magnesium dihydrogen phosphate, magnesium hydrogen phosphate, magnesium phosphate, magnesium ammonium phosphate, magnesium ammonium phosphate hexahydrate, strontium phosphate, strontium hydrogen phosphate, strontium dihydrogen phosphate, and a mixture thereof.

According to one embodiment, the main constituent is a sulfate selected from the group consisting of, calcium sulfate dihydrate, calcium sulfate hemihydrate, calcium sulfate anhydrate, magnesium sulfate, magnesium sulfate monohydrate, magnesium sulfate heptahydrate, strontium sulfate, and a mixture thereof.

According to one embodiment, in the bone cement composition kit of the present disclosure, the bone matrix component comprises the bone matrix and a vehicle. Preferably, the bone matrix component is provided in the bone cement composition kit in the form of clay, granule, or powder. More preferably, the bone matrix component is provided in the bone cement composition kit as clay.

According to one embodiment, various biocompatible vehicles may be used to support the bone matrix component or the hydrogel component in the bone cement composition kit of the present disclosure; and the vehicles may also be used to increase the viscosity thereby endowing a desired plasticity to the bone matrix component or the hydrogel component in the bone cement composition kit. The selection of a suitable vehicle depends on the size of the granule, the volume to be filled, the size of the needle, and the property of the filler. According to one embodiment, examples of the vehicle include, but are not limited to, cellulose, cellulose derivatives, glycerol, polyethylene glycol (PEG), glycosaminoglycan, collagen, gelatin, ethylene glycol, propylene glycol, polyhydroxyalkanoate (PHA), polylactic acid (PLA), polyglycolic acid (PGA), poly(lactic-co-glycolic acid) (PLGA), polycaprolactone (PCL), and a mixture thereof. According to one embodiment, the cellulose derivatives is selected from the group consisting of methyl cellulose, sodium carboxymethyl cellulose, carboxymethyl cellulose (CMC), hydroxyethyl cellulose (HEC), ethyl cellulose, hydroxypropyl cellulose (HPC), hydroxypropyl methyl cellulose (HPMC), and a mixture thereof. According to one embodiment, the polyethylene glycol (PEG) is selected from the group consisting of polyethylene glycol 600 (PEG600), polyethylene glycol 4000 (PEG4000), and a mixture thereof. According to one embodiment, the glycosaminoglycan is selected from the group consisting of hyaluronan, chondroitin sulfate and derivatives thereof, and a mixture thereof.

According to one embodiment, in the bone cement composition kit of the present disclosure, the bone matrix may be mixable with said vehicle to form a bone matrix component comprising the bone matrix.

According to one embodiment, in the bone cement composition kit of the present disclosure, the hydrogel component comprises an acrylic polymer, which is formed by the polymerization of acrylic monomer as the polymerizable monomer, examples of which include, but are not limited to, (A) poly(alkyl acrylates) such as such as, poly(methyl methacrylate)(PMMA), poly(ethyl methacrylate) (PEMA), poly(butyl methacrylate) (PBMA), poly(methyl acrylate) (PMA), etc.; these polymers are formed from the polymerization of alkyl acrylate-based monomer, such as, methyl acrylate (MA), methyl methacrylate (MMA), ethyl methacrylate (EMA), butyl methacrylate, etc.; (B) copolymers formed from the copolymerization of methyl acrylate (MA) or methyl methacrylate with at least one monomer selected from styrene, ethyl methacrylate, and methyl acrylate; and (C) polymers formed from the polymerization of dimethyl acrylate-based monomer, such as bisphenol A-diglycidyl dimethacrylate (Bis-GMA), 2,2-bis[4-(3-methyl propenoxy-2-hydroquinone propoxyl)phenyl]propane, 2,2-bis(4-methylpropenoxyethoxyphenyl)propane (Bis-MEPP), triethylene glycol dimethacrylate (TEGDMA), diethylene glycol dimethacrylate (DEGDMA), ethylene glycol dimethacrylate (EGDMA), etc. According to one embodiment, the bone cement composition kit of the present disclosure preferably comprises poly(methyl methacrylate) or copolymers formed using methyl methacrylate as the polymerizable monomer.

According to one embodiment, in the bone cement composition kit of the present disclosure, the hydrogel component comprises an acrylic monomer, in which the acrylic monomer is mixable with the above-mentioned acrylic polymer to form the hydrogel, thereby allowing the polymerization of the polymerizable monomer (such as, methyl acrylate monomer), which in turn hardens the bone cement composition. Illustrative examples of the acrylic monomer include, but are not limited to, alkyl acrylate-based monomer, dimethyl acrylate-based monomer, etc. Preferred examples of the acrylic monomer are methyl methacrylate (MMA), ethyl methacrylate (EMA), butyl methacrylate, methyl acrylate (MA), etc. Preferred examples of the dimethyl acrylate-based monomer are bisphenol A-diglycidyl dimethacrylate (Bis-GMA), 2,2-bis[4-(3-methyl propenoxy-2-hydroquinone propoxyl)phenyl]propane, 2,2-bis(4-methylpropenoxyethoxy)phenyl) propane (Bis-MEPP), triethylene glycol dimethacrylate (TEGDMA), diethylene glycol dimethacrylate (DEGDMA), ethylene glycol dimethacrylate (EGDMA), etc.

According to one embodiment, in the bone cement composition kit of the present disclosure, the acrylic polymer may be mixable with a vehicle to form a hydrogel component comprising the acrylic polymer. According to one embodiment, illustrative examples of the vehicle include, but are not limited to, cellulose, cellulose derivatives, glycerol, polyethylene glycol (PEG), glycosaminoglycan, collagen, gelatin, ethylene glycol, propylene glycol, polyhydroxyalkanoate (PHA), polylactic acid (PLA), polyglycolic acid (PGA), poly(lactic-co-glycolic acid) (PLGA), polycaprolactone (PCL), and a mixture thereof. According to one embodiment, the cellulose derivatives is selected from the group consisting of methyl cellulose, sodium carboxymethyl cellulose, carboxymethyl cellulose (CMC), hydroxyethyl cellulose (HEC), ethyl cellulose, hydroxypropyl cellulose (HPC), hydroxypropyl methyl cellulose (HPMC), and a mixture thereof. According to one embodiment, the polyethylene glycol (PEG) is selected from the group consisting of polyethylene glycol 600 (PEG600), polyethylene glycol 4000 (PEG4000), and a mixture thereof. According to one embodiment, the glycosaminoglycan is selected from the group consisting of hyaluronan, chondroitin sulfate and derivatives thereof, and a mixture thereof.

According to one embodiment, the bone cement composition kit of the present disclosure further comprises a polymerization initiator and a polymerization promoter capable of promoting the polymerization of the acrylic polymer with the proviso that the polymerization initiator and the polymerization promoter are not provided in the same component at the same time.

According to one embodiment, in the bone cement composition kit of the present disclosure, the polymerization initiator may be provided in the bone matrix component comprising the bone matrix or the hydrogel component.

According to one embodiment, in the bone cement composition kit of the present disclosure, the polymerization promoter may be provided in the bone matrix component comprising the bone matrix or the hydrogel component.

According to one embodiment, in the bone cement composition kit of the present disclosure, the acrylic polymer and the acrylic monomer are first mixed to form the hydrogel, and before the bone matrix component and hydrogel are mixed using a dual-cylinder device, the polymerization initiator and the polymerization promoter are individually added into the bone matrix component and the hydrogel component. In this way, only when a mixture is injected using the dual-cylinder, will the polymerization initiator and the polymerization promoter come into contact and trigger the polymerization, whereas the portion that is not injected will not be polymerized. Accordingly, the operating time could be extended, thereby improving the disadvantage of the limited operating time of the conventional bone cement.

According to one embodiment, illustrative examples of the polymerization initiator include, but are not limited to, benzoyl peroxide (BPO), tert-butyl hydroperoxide, lauroyl peroxide, azobisisobutyronitrile, and a mixture thereof. According to one embodiment, the polymerization initiator is preferably BPO.

According to one embodiment, illustrative examples of the polymerization promoter include, but are not limited to, N,N-dimethyl-p-toluidine, 2,4,6-tris(dimethylaminomethyl) phenol, and a mixture thereof. According to one embodiment, the polymerization promoter is preferably N,N-dimethyl-p-toluidine.

According to one embodiment, in the bone cement composition kit of the present disclosure, the hydrogel component may further comprise a polymerization inhibitor. Illustrative examples of the polymerization inhibitor include, but are not limited to, hydroquinone (HQ), methyl hydroquinone (MEHQ), and ascorbic acid.

According to one embodiment, in the bone cement composition kit of the present disclosure, the bone matrix component or the hydrogel component may further comprise a developing agent. Illustrative examples of the developing agent include, but are not limited to, barium sulfate, zirconium oxide, thallium, titanium dioxide, $^{153}$Sm, triphenylbismuthin iodixanol, and iohexol.

According to one embodiment, in the bone cement composition kit of the present disclosure, the bone matrix component or the hydrogel component may further comprise small-molecule osteoinductive drugs, such as corticosteroids, oxidized steroids, etc.

According to one embodiment, in the bone cement composition kit of the present disclosure, the bone matrix component or the hydrogel component may further comprise an osteogenic material, such as, living cell sources, e.g., stem cells, multipotent cells, pluripotent cells, osteoprogenitor cells, preosteoblasts, mature osteoblasts, and a mixture thereof, and the like.

According to one embodiment, the bone cement composition kit of the present disclosure may be used to prepare a medical composition for treating bone defects. According to one embodiment, the medical composition prepared using the bone cement composition kit of the present disclosure can be used to repair and fill various bone defects. According to one embodiment, the term "bone defect" refers to any bone regions with a defect, such as voids, cracks, notches, or any other discontinuity in the bone. For example, said bone defect may be caused by any of the following factors, osteoporotic vertebral compression fractures, ischemic bone necrosis, cavity within the spinal cord caused by benign or malignant osteoma, bone collapse, deformation of the bone structure, bone defects resulted from traumas, bone defects resulted from limb or craniofacial surgeries, etc.

As could be appreciated by persons having ordinary skill in the art, in addition to those described in the previous embodiments, the bone cement composition kit of the present disclosure can be used in many other applications. Persons having ordinary skill in the art should also understand that these detailed descriptions and appended drawings are provided for the illustrative purpose and shall not be construed as limiting to the scope of the present invention. Those skilled in the art should also realize that they may make various changes, substitutions, and alterations herein without departing from the spirit and scope of the present disclosure. The scope of the present disclosure shall only be limited to the appended claims.

DETAILED DESCRIPTION

Specific examples of the present disclosure are provided below; however, the present disclosure is not limited to these specific examples.

In the following specific examples, the amount of each component is expressed as the weight percent (wt %).

Example I

Preparation of Bone Cement Composition 1

13.2% glycerol, 18.0% PEG600, 18.0% PEG 4000, 10.8% CMC, 30.0% tricalcium phosphate (TCP), and 10.0% N,N-dimethyl-p-toluidine (DMPT) were mixed to form a clay component.

Further, 24.79% PMMA, 29.08% barium sulfate, 1.63% TCP, 2.62% benzoyl peroxide (BPO), 0.05% hydroquinone (HQ) and 41.83% methyl methacrylate (MMA) were mixed to form an acrylic hydrogel component. The viscosity of the PMMA was 145 ml/g with a central particle size of 55 μm and having 0.4% BPO.

Last, in a dual-cylinder injector with a volume ratio of 10:1, the bone matrix component was filled into the cylinder with the smaller volume, and the acrylic hydrogel component was filled into the other cylinder with the greater volume. A combining nozzle was installed on the dual-cylinder syringe, and the injection started at a temperature of 23° C.±1° C. The bone cement composition injected from the dual-cylinder syringe was also referred to as the bone cement composition 1.

The time point at which the injected bone cement composition 1 was in an un-runny state was recorded, and this time point was designated as the starting point of the injection operation. The injectability of the bone cement composition 1 was tested every 30 seconds, and the time point at which the composition was no longer injectable was recorded and used as the stop point of the injection operation. Meanwhile, the injected bone cement composition 1 was filled into a mold and made into five cylinders having the size of 12 mm (length)×6 mm (diameter); the molded cylinders were stood for 24 hours and then subjected to ISO-5833 test to determine the compressive strength thereof.

The injection period for the bone cement composition 1 was 0 minute to more than one hour; the compressive strength thereof was 70.5±3.9 MPa.

Since the acrylic hydrogel did not contain DMPT, the acrylic hydrogel itself did not harden, and only the injected mixture hardened. Since the acrylic hydrogel and bone matrix component are both prepared by the manufacturer, the user does not have to perform any mixing, and therefore, during the handling operation, the viscosity of the composition does not increase; accordingly, the present bone cement composition provides a stable handleability and is easy to use, and does not produce the MMA vapor that is harmful to the medical caretakers.

Example II

Preparation of Bone Cement Composition 2

21.0% glycerol, 21.0% PEG600, 16.0% PEG 4000, 6.0% CMC, 26.0% TCP, and 10.0% DMPT were mixed to form a clay component.

Further, 30.22% PMMA, 26.17% barium sulfate, 1.74% BPO, 0.03% HQ, and 41.83% MMA were mixed to form an acrylic hydrogel component. The viscosity of the PMMA was 90 ml/g with a central particle size of 40 μm and having 5% BPO.

Last, in a dual-cylinder injector with a volume ratio of 4:1, the bone matrix component was filled into the cylinder with the smaller volume, whereas the acrylic hydrogel component was filled into the other cylinder with the greater volume. A combining nozzle was installed on the dual-cylinder syringe, and the injection started at a temperature of 23° C.±1° C. The bone cement composition injected from the dual-cylinder syringe was also referred to as the bone cement composition 2.

The time point at which the injected bone cement composition 2 was in an un-runny state was recorded, and this time point was designated as the starting point of the injection operation. The injectability of the bone cement composition 2 was tested every 30 seconds, and the time point at which the composition was no longer injectable was recorded and used as the stop point of the injection operation. Meanwhile, the injected bone cement composition 2 was filled into a mold and made into five cylinders having the size of 12 mm (length)×6 mm (diameter); the molded cylinders were stood for 24 hours and then subjected to ISO-5833 test to determine the compressive strength thereof.

The injection period for the bone cement composition 2 was 0 minute to more than one hour; the compressive strength thereof was 41.1±2.3 MPa.

Example III

Preparation of Bone Cement Composition 3

21.0% glycerol, 21.0% PEG600, 16.0% PEG 4000, 6.0% CMC, 26.0% TCP, and 10.0% DMPT were mixed to form a clay component.

Further, 30.22% PMMA, 26.17% barium sulfate, 1.74% BPO, 0.03% HQ and 41.83% MMA were mixed to form an acrylic hydrogel component. The viscosity of the PMMA was 90 ml/g with a central particle size of 40 μm and having 5% BPO.

Last, in a dual-cylinder injector with a volume ratio of 2:1, the bone matrix component was filled into the cylinder with the smaller volume, whereas the acrylic hydrogel component was filled into the other cylinder with the greater volume. A combining nozzle was installed on the dual-cylinder syringe, and the injection started at a temperature of 23° C.±1° C. The bone cement composition injected from the dual-cylinder syringe was also referred to as the bone cement composition 3.

The time point at which the injected bone cement composition 3 was in an un-runny state was recorded, and this time point was designated as the starting point of the injection operation. The injectability of the bone cement composition 3 was tested every 30 seconds, and the time point at which the composition was no longer injectable was recorded and used as the stop point of the injection operation. Meanwhile, the injected bone cement composition 3 was filled into a mold and made into five cylinders having the size of 12 mm (length)×6 mm (diameter); the molded cylinders were stood for 24 hours and then subjected to ISO-5833 test to determine the compressive strength thereof.

The injection period for the bone cement composition 3 was 0 minute to more than one hour; the compressive strength thereof was 23.8±1.2 MPa.

What is claimed is:

1. A bone cement composition kit, comprising a bone matrix component and a hydrogel component, respectively stored in separate containers of a dual-cylinder device, wherein the bone matrix component and the hydrogel component are mixed by the dual-cylinder device, wherein the bone matrix component comprises a bone matrix, wherein the bone matrix has a main constituent selected from phosphates, sulfates, bioglass ($Na_2O$—$CaO$—$SiO_2$—$P_2O_5$), and a mixture thereof, the hydrogel component comprises an acrylic polymer and an acrylic monomer, and the ratio of the bone matrix component to the hydrogel component is in a range from about 1:2 (ml/ml) to 1:10 (ml/ml).

2. The bone cement composition kit of claim 1, wherein the bone matrix component further comprises a vehicle, wherein the vehicle is selected from the group consisting of cellulose, cellulose derivatives, glycerol, polyethylene glycol (PEG), glycosaminoglycan, collagen, gelatin, ethylene glycol, propylene glycol, polyhydroxyalkanoate (PHA), polylactic acid (PLA), polyglycolic acid (PGA), poly(lactic-co-glycolic acid) (PLGA), polycaprolactone (PCL), and a mixture thereof.

3. The bone cement composition kit of claim 2, wherein the cellulose derivatives is selected from the group consisting of methyl cellulose, sodium carboxymethyl cellulose, carboxymethyl cellulose (CMC), hydroxyethyl cellulose (HEC), ethyl cellulose, hydroxypropyl cellulose (HPC), hydroxypropyl methyl cellulose (HPMC), and a mixture thereof; the polyethylene glycol (PEG) is selected from the group consisting of polyethylene glycol 600 (PEG600), polyethylene glycol 4000 (PEG4000), and a mixture thereof; and the glycosaminoglycan is selected from the group consisting of hyaluronan, chondroitin sulfate and derivatives thereof, and a mixture thereof.

4. The bone cement composition kit of claim 1, wherein the bone matrix component is provided in the bone cement composition kit in the form of clay, granule, or powder.

5. The bone cement composition kit of claim 1, wherein the ratio of the acrylic polymer to the acrylic monomer is in a range from about 1:10 (g/g) to about 20:1 (g/g).

6. The bone cement composition kit of claim 1, further comprising a polymerization initiator and a polymerization promoter with the proviso that the polymerization initiator and the polymerization promoter are not provided in the same component at the same time.

7. The bone cement composition kit of claim 6, wherein the polymerization initiator is selected from the group consisting of benzoyl peroxide, tert-butyl hydroperoxide, lauroyl peroxide, azobisisobutyronitrile, and a mixture thereof.

8. The bone cement composition kit of claim 6, wherein the polymerization promoter is selected from the group consisting of N,N-dimethyl-p-toluidine, 2,4,6-tris(dimethylaminomethyl)phenol, and a mixture thereof.

9. The bone cement composition kit of claim 1, further comprising a polymerization inhibitor, wherein the polymerization inhibitor is provided in the hydrogel component.

10. The bone cement composition kit of claim 1, wherein the main constituent is a phosphate selected from the group consisting of, hydroxyapatite (HA), β-tricalcium phosphate (β-TCP), tetracalcium phosphate, calcium hydrogen phosphate ($CaHPO_4$), octacalcium phosphate ($Ca_8H_2(PO_4)_6 \cdot 5H_2O$), calcium pyrophosphate ($Ca_2P_2O_7$), amorphous calcium phosphate (ACP), magnesium dihydrogen phosphate, magnesium hydrogen phosphate, magnesium phosphate, magnesium ammonium phosphate, magnesium ammonium phosphate hexahydrate, strontium phosphate, strontium hydrogen phosphate, strontium dihydrogen phosphate, and a mixture thereof.

11. The bone cement composition kit of claim 1, wherein the main constituent is a sulfate selected from the group consisting of calcium sulfate dihydrate, calcium sulfate hemihydrate, calcium sulfate anhydrate, magnesium sulfate, magnesium sulfate monohydrate, magnesium sulfate heptahydrate, strontium sulfate, and a mixture thereof.

12. The bone cement composition kit of claim 1, wherein the acrylic polymer is selected from the group consisting of (A) poly(alkyl acrylates) formed from the polymerization of alkyl acrylate-based monomers; (B) copolymers formed from the copolymerization of methyl acrylate or methyl methacrylate with at least one monomer selected from styrene, ethyl methacrylate, and methyl acrylate; and (C) polymers formed from the polymerization of dimethyl acrylate-based monomers.

13. The bone cement composition kit of claim 1, wherein the acrylic monomer is selected from the group consisting of methyl methacrylate (MMA), ethyl methacrylate (EMA), butyl methacrylate, methyl acrylate (MA), bisphenol A-diglycidyl dimethacrylate (Bis-GMA), 2,2-bis[4-(3-methyl propenoxy-2-hydroquinone propoxyl)phenyl]propane, 2,2-bis(4-methylpropenoxyethoxyphenyl)propane (Bis-MEPP), triethylene glycol dimethacrylate (TEGDMA), diethylene glycol dimethacrylate (DEGDMA), ethylene glycol dimethacrylate (EGDMA), and a combination thereof.

14. A method of treating a bone defect comprising administrating to a bone region with defect the bone cement composition kit of claim 1.

* * * * *